United States Patent
Bagley et al.

(10) Patent No.: US 6,228,245 B1
(45) Date of Patent: May 8, 2001

(54) PROCESS FOR THE PREPARATION OF TETRAALKYL 1,2,3,4-BUTANETETRACARBOXYLATES

(75) Inventors: Melvin R. Bagley, St. Louis, MO (US); Monica C. Dutton, Pensacola, FL (US); Dennis J. Kalota, Fenton, MO (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 09/101,591

(22) PCT Filed: Jan. 10, 1997

(86) PCT No.: PCT/US97/00400

§ 371 Date: Oct. 5, 1999

§ 102(e) Date: Oct. 5, 1999

(87) PCT Pub. No.: WO97/25452

PCT Pub. Date: Jul. 17, 1997

Related U.S. Application Data

(60) Provisional application No. 60/009,641, filed on Nov. 11, 1996.

(51) Int. Cl.$^7$ .................... C25B 3/00; C25B 3/10
(52) U.S. Cl. ............................... 205/440; 205/415
(58) Field of Search ..................... 205/440, 415

(56) References Cited

U.S. PATENT DOCUMENTS

| | | | |
|---|---|---|---|
| 3,193,475 | * | 7/1965 | Baizer ........................ 204/73 |
| 3,193,510 | * | 7/1965 | Baizer ........................ 252/363.5 |
| 4,814,510 | * | 3/1989 | Degner et al. ................. 568/425 |
| 5,244,546 | * | 9/1993 | Casanova et al. ............... 204/59 R |
| 5,248,396 | * | 9/1993 | Casanova et al. ............... 204/59 R |
| 5,298,653 | * | 3/1994 | Casanova et al. ............... 562/590 |
| 5,364,964 | * | 11/1994 | Casanova et al. ............... 562/590 |

FOREIGN PATENT DOCUMENTS

0433260 * 6/1991 (EP) .

OTHER PUBLICATIONS

Organic Electrochemistry, 2$^{nd}$ ed. Baizer & Lund, Ed., Marcel Dekker, Inc., New York, New York, 1983, pp. 669 and 672, no month available.*

Journal of the Electrochemical Society, 114(10), pp. 1024–1025, 1967, Baizer & Lund, no month available.*

*Collection of Czech Chem Communications*, Sazou et al., vol. 52, 1987, pp. 2132–2141, no month available.*

Electrochimica Acta, Electrolytic Reductive Coupling as a Synthetic Tool, vol. 12 No. 9, Sep. 1967, M.M. Baizer, et al., pp. 1377, 1380, and 1381.*

* cited by examiner

*Primary Examiner*—Edna Wong
(74) *Attorney, Agent, or Firm*—Thompson Coburn LLP; Greg Upchurch; Paul A. Lesko

(57) ABSTRACT

Electrolytic hydrodimeric coupling of dialkyl maleates in alkanol solutions containing an alkanol-soluble alkali metal alkoxide/quaternary ammonium tetrafluoroborate mixed supporting electrolyte yields tetraalkyl 1,2,3,4-butanetetracarboxylates.

19 Claims, No Drawings

PROCESS FOR THE PREPARATION OF TETRAALKYL 1,2,3,4-BUTANETETRACARBOXYLATES

This application is a 371 Entry of the U.S. Patent office of PCT/US97/00400 claims priority of U.S. patent application Ser. No. 60/009,641, filed Nov. 11, 1996.

BACKGROUND OF THE INVENTION

1. Field of the Invention

This invention relates to an electrolytic process for the preparation of tetraalkyl 1,2,3,4-butanetetracarboxylates from dialkyl maleates. The products are useful as precursors of the corresponding free acid, 1,2,3,4-butanetetracarboxylic acid. Conversion of the tetraalkyl 1,2,3,4-butanetetracarboxylates into the corresponding free acid can be effected as described and claimed in commonly assigned U.S. Pat. No. 5,298,653. This reference is herein incorporated by reference.

The corresponding free acid, 1,2,3,4-butanetetracarboxylic acid, has been found by the U.S. Department of Agriculture to be an effective permanent press agent for polyester-cotton blend fabrics, and could find use in large quantities for such purpose. Accordingly, an efficient process for the preparation of the free acid is deemed highly desirable and useful. A requirement of any such process, however, is that it must produce a product exhibiting acceptable color performance properties, as this is a critical factor for suitability for permanent press agents.

2. Description of the Related Art

Electrolytic reductive couplings of various activated olefins have been investigated and reported in the art. Much of this work involved aqueous systems in a divided cell, and often with a supporting electrolyte salt with a very negative discharge potential, such as a quaternary ammonium salt. In addition, however, to the desired reductive coupling reaction, other undesired side reactions such as, for example, simple reduction and polymerization frequently occur. Various parameters of such reactions have been discussed, including the use of various supporting electrolytes. See *Organic Electrochemistry*, 2nd ed, Baizer and Lund, Ed., Marcel Dekker, Inc., New York, N.Y., 1983. At page 669 of this reference, for example, it is stated that undivided cells are operable with the restrictions that (i) the olefin and reaction product not be substantially oxidized at the anode, and (ii) the oxygen evolved at the anode in aqueous systems not promote undesirable side reactions. In addition, at pages 669 and 672, reference is made to dimerization of diethyl maleate and the effect of alkali metal cations in increasing the rate of dimerization of anion radicals.

Electrolytic hydrodimerization, also referred to as electrohydrodimerization, of diethyl maleate has been reported by Baizer et al, *Journal of the Electrochemical Society*, 114(10), 1024–1025 (1967). In accordance with the described procedures, the electrolyses were carried out using a catholyte of water and dimethylformamide in a divided electrolysis cell. The reference further indicated that, all other conditions being equal, more hydrodimerization occurs in the presence of tetraethylammonium ion than of sodium ion. The electrolyses were carried out for three (3) hours, generally resulting in about 50% conversions, and specified amounts of hydrodimer, and other products.

Methanol has been employed as a solvent for the study of reduction mechanisms. In Sazou et al, *Collections of Czechoslovakia Chemical Communications*, 52, 2132–2141 (1957), cyclic voltammograms of dilute methanol solutions—for example, 0.0025 or 0.005 mole/liter—of maleic acid and fumaric acid with various supporting electrolytes, employing a hanging mercury electrode, are presented, and reduction mechanisms discussed. The reference postulates that the double bond reduction of the corresponding dimethyl esters of maleic acid and fumaric acid occurs in one step.

Electrohydimerization of dialkyl maleates is known in the art. In U.S. Pat. No. 5,244,546, a process is described for the electrolytic reductive coupling of dialkyl maleates to yield tetraalkyl 1,2,3,4-butanetetracarboxylates. In accordance with the process, the electrohydrodimerization is carried out by subjecting an electrolysis medium comprising a substantial concentration of the dialkyl maleate in a substantially anhydrous alkanol, and a supporting electrolyte to electrolysis in an undivided electrolysis cell. The reaction reportedly results in good yields of tetraalkyl 1,2,3,4-butanetetracarboxylates.

In many instances, however, particularly in a commercial scale process, a small percent increase in the yield of the desired product, relative to known processes, represents a tremendous economic advantage. Accordingly, research efforts are continually being made to define new or improved processes for preparing new and old desired products. The discovery of the process of the instant invention, therefore, is believed to constitute a decided advance in the electrohydrodimerization art.

SUMMARY OF THE INVENTION

The instant invention is directed to an electrolytic hydrodimerization preparative process for tetraalkyl 1,2,3,4-butanetetracarboxylates. Accordingly, the primary object of the instant invention is to provide an improved electrohydrodimerization process for the electrolytic hydrodimeric coupling of dialkyl maleates in an alkanol-containing liquid electrolysis medium.

This and other objects, aspects, and advantages of the instant invention will become apparent to those skilled in the art from the accompanying description and claims.

The above objects are achieved by the process of the instant invention which comprises subjecting a substantially anhydrous liquid electrolysis medium containing a dialkyl maleate, an alkanol-soluble alkali metal alkoxide/quaternary ammonium tetrafluoroborate mixed supporting electrolyte to electrolysis in an electrolysis cell fitted with a graphite anode and a graphite cathode to effect electrohydrodimerization of the dialkyl maleate to yield the corresponding tetraalkyl 1,2,3,4-butanetetracarboxylate.

The tetraalkyl 1,2,3,4-butanetetracarboxylates obtained in the process of the instant invention can be readily recovered by any of a number of conventional and well-known recovery procedures known in the art. Worthy of particular note are procedures described in commonly assigned U.S. Pat. No. 5,248,396, which reference is herein incorporated by reference.

DESCRIPTION OF THE PREFERRED EMBODIMENTS

Electrolytic hydrodimeric coupling of dialkyl maleates in alkanol solutions containing an alkanol-soluble alkali metal alkoxide/quaternary ammonium tetrafluoroborate mixed supporting electrolyte provides excellent selectivities to, and yields of, tetraalkyl 1,2,3,4-butanetetracarboxylates. In accordance therewith, an electric current is passed through a substantially anhydrous liquid electrolysis medium containing the dialkyl maleate, an alkanol corresponding to the alkyl groups of the dialkyl maleate, and an alkanol-soluble alkali metal alkoxide/quaternary ammonium tetrafluoroborate mixed supporting electrolyte contained in an electrolysis cell fitted with a graphite anode and a graphite cathode to cause hydrodimeric coupling of the dialkyl maleate to yield the corresponding tetraalkyl 1,2,3,4-butanetetracarboxylate. The process generally involves use of a liquid electrolysis medium having a very substantial concentration of the dialkyl maleate reactant and use of fairly substantial electrical current in the electrolysis, and obtaining substantial amounts of the corresponding tetraalkyl 1,2,3,4-butanetetracarboxylate product in a reasonable reaction time.

The process of the instant invention can be conducted with dialkyl maleates in general. But, for practical considerations, only the dialkyl maleates wherein the alkyl groups of the ester functionalities are lower alkyl groups, for example, alkyl groups of 1 to 6 carbon atoms, are likely to be of significant interest. In addition, it will be noted that since there are two alkyl groups contained in the ester functionalities of the dialkyl maleates, the alkyl groups can be the same or different. But, again for practical considerations, it is preferred that both such alkyl group be the same. In such manner, the choice of a suitable alkanol solvent is resolved without undue additional considerations.

Among the dialkyl maleates, dimethyl maleate is the preferred reactant, and is used herein to exemplify the process of the instant invention. However, diethyl maleate, di-n-propyl maleate, diisopropyl maleate, di-n-butyl (and isomers thereof) maleate, di-n-pentyl (and isomers thereof) maleate, and di-n-hexyl (and isomers thereof) maleate are also suitable for use in the process of the instant invention. It is recognized, however, that electrical resistance tends to increase with increasing alkyl size, whether in the ester or in the alkanol solvent, thereby making electrical power usage less efficient. A further disadvantage of high molecular weight alkanols is that they tend to be solids at ambient temperatures, thereby requiring elevated temperatures to provide a liquid electrolysis medium.

The term "and isomers thereof" following the names of various alkyl groups of the ester functionalities of the dialkyl maleates is employed herein to designate the isomers of the preceding alkyl group. For example, "and isomers thereof" following "di-n-butyl" designates isomeric butyl groups (other than the expressly named n-butyl), such as isobutyl, sec-butyl, and tert-butyl. Thus, the term "di-n-butyl (and isomers thereof) maleate" designates di-n-butyl maleate, diisobutyl maleate, di-sec-butyl maleate, and di-tert-butyl maleate.

Alkanols suitable for use in the process of the instant invention are those which contain an alkyl group corresponding to the alkyl group of the dialkyl maleate. This requirement avoids the difficulty associated with ester interchange with the dialkyl maleates. For practical reasons, however, as with the dialkyl maleates, only alkanols wherein the alkyl group is a lower alkyl group, for example, alkyl groups of 1 to 6 carbon atoms, are likely to be of significant interest. Exemplary of suitable alkanols are methanol, ethanol, 1-propanol, 2-propanol (isopropyl alcohol), 1-butanol, 2-butanol (sec-butyl alcohol), 2-methyl-1-propanol (isobutyl alcohol), 2-methyl-2-propanol (tert-butyl alcohol), 1-pentanol, 2-pentanol (sec-amyl alcohol), 3-pentanol, 3-methyl-1-butanol, 3-methyl-2-butanol, 2-methyl-2-butanol, 2,2-dimethyl-1-propanol, and the like. Among these alcohols, methanol is generally preferred in that it (a) has the highest dielectric constant of the simple alcohols, (b) is the least expensive of the simple alcohols, (c) gives higher current efficiencies than do the higher simple alcohols, (d) is a liquid at ambient temperatures and thereby readily provides a liquid electrolysis medium, (f) facilitates the use of dimethyl maleate as the dialkyl maleate of choice, and (f) is relatively easily separated from the desired tetraalkyl 1,2,3,4-butanetetracarboxylate product, tetramethyl 1,2,3,4-butanetetracarboxylate.

As previously noted in the Background of the Invention, an important use for tetraalkyl 1,2,3,4-butanetetracarboxylates involves its conversion to 1,2,3,4-butanetetracarboxylic acid, which, in turn, finds utility as an effective permanent press agent for polyester-cotton blend fabrics. For this purpose, the simplest ester, tetramethyl 1,2,3,4-butanetetracarboxylate, serves very well and is generally preferred. As a result, there will ordinarily be no reason to choose other tetraalkyl esters as intermediates for the same product.

While not desiring to be bound by the theory of the instant invention, or to limit the invention in any way, it is believed that Reactions (1), (2), and (3) show the reactions involved, the reaction of dimethyl maleate in methanol to prepare tetramethyl 1,2,3,4-butanetetracarboxylate being used for purposes of illustration.

(1)

Cathode Reaction:

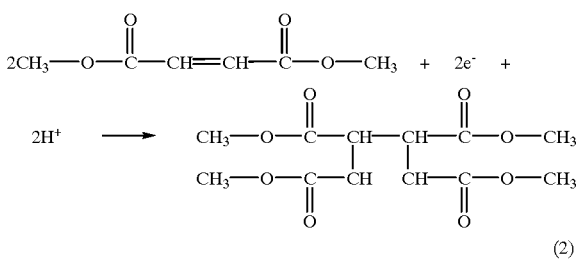

(2)

Anode Reaction:

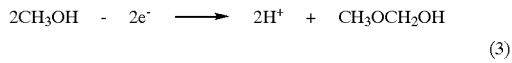

(3)

Sum of Reactions (1) and (2):

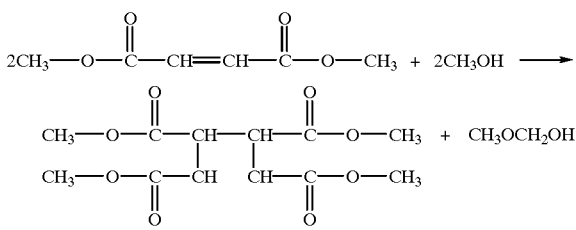

Methoxymethanol, the presumed reaction product at the anode, is the hemiacetal of formaldehyde. The presence of formaldehyde in the product mixture has been confirmed, but it may be formed by the disassociation of methoxymethanol. Additional possible intermediates include ·CH$_2$OH and ·CH$_2$OH in the anode reaction, and methanol from protons and methoxide ion (employed as a component of the supporting electrolyte). Also, alkoxides, e.g., methoxide (CH$_3$O· or MeO·), can be produced from reaction of alkanol, e.g., CH$_3$OH or MeOH, at the cathode.

The presence of ·CH$_2$OH as a likely intermediate at the anode presents the possibility for the addition of such intermediate at the double bond of the dialkyl maleate to cause production of undesired by-products, thereby possibly causing considerable loss in selectivity to the desired hydrodimer, tetraalkyl 1,2,3,4-butanetetracarboxylate, particularly when an undivided electrolysis cell is used. However, such undesired side reaction does not occur to any significant and/or substantial extent in that good results, i.e., good selectivities and yields of the desired hydrodimer, are obtained in the preferred undivided electrolysis cell. In fact, it is believed that the use of an undivided electrolysis cell is advantageous, as it permits protons generated at the anode to move very freely throughout the electrolysis medium to protonate alkoxide, e.g., methoxide, ions generated in conjunction with the hydrodimerization at the cathode, thereby avoiding possible interfering reactions of the alkoxide ions and polymerization.

In accordance with the process of the instant invention it has been discovered that electrolytic hydrodimerization reaction is carried our effectively and efficiently with a mixed supporting electrolyte. Indeed, it has been discovered that the employment of the mixed supporting electrolyte in accordance with the process of the instant invention results in unexpectedly high selectivities to, and yields of, the desired hydrodimer, tetraalkyl 1,2,3,4-butanetetracarboxylate.

It will be apparent to those having ordinary skill in the art that the alkanol-based electrolysis medium must have sufficient conductivity to conduct the required electric current. And although media of less than ideal conductivity can be employed, it is preferred from an economic viewpoint not to have too high a resistance, thereby avoiding substantial inefficiencies in electric current usage. Having in mind the desire to minimize inefficiencies in electric usage, the conductivity of the electrolysis medium is enhanced by the addition of suitable supporting electrolytes, e.g., electrolyte salts having sufficiently high discharge potentials, to the alkanol-based electrolysis medium.

The term "supporting electrolyte" is employed herein to mean an electrolyte capable of carrying electric current but not discharging under electrolysis conditions. It will be recognized, however, that discharge potentials will vary with electrode materials and their surface conditions and various materials in the electrolysis medium.

The term "salt" is employed in its generally recognized sense to mean a compound composed of a cation and an anion, e.g., the reaction product of an acid and a base.

An alkanol-soluble mixed supporting electrolyte is employed in the process of the instant invention to enhance the conductivity of the electrolysis medium. In accordance with the present process, the mixed supporting electrolyte comprises an alkali metal alkoxide and a quaternary ammonium tetrafluoroborate. The alkali metal alkoxide/quaternary ammonium tetrafluoroborate mol ratio is between about 0.5/1 to about 5/1, with a mol ratio of about 1/1 being preferred.

Among the alkali metal alkoxides, suitable cations include lithium, sodium, potassium, rubidium, and cesium, with lithium, sodium, and potassium being preferred, and sodium generally being most preferred. Suitable alkoxide anions include those containing lower alkyl groups, for example, alkyl groups of 1–6 carbon atoms. Exemplary of the alkoxide anions are methoxide, ethoxide, n-propoxide, isopropoxide, n-butoxide (and isomers thereof), n-pentoxide (and isomers thereof), and n-hexoxide (and isomers thereof). As a practical matter, however, it is preferred to employ an alkoxide anion which corresponds to the alkanol solvent.

In the manner noted in connection with the term "and isomers thereof" following the names of various alkyl groups of the ester functionalities of the dialkyl maleates, the term "and isomers thereof" following the names of various alkoxide anions of the alkali metal alkoxide supporting electrolyte is employed herein to designate the isomers of the preceding alkoxide anion. For example, "and isomers thereof" following "n-butoxide" designates isomeric butoxide anions (other than the expressly named n-butoxide), such as isobutoxide, sec-butoxide, and tert-butoxide. Thus, the term "n-butoxide (and isomers thereof)" designates n-butoxide, isobutoxide, sec-butoxide, and tert-butoxide.

Non-limiting examples of suitable quaternary ammonium cations of the quaternary ammonium tetrafluoroborates include the tetraalkylammonium cations, e.g., tetramethylammonium, tetraethylammonium, tetra-n-propylammonium, tetraisopropylammonium, tetra-n-butylammonium, tetraisobutylammoniuum, tetratert-butylammonium, and the like, heterocyclic and alkylarylammonium cations, e.g., phenyltriethylammonium and the like, with the tetraalkylammonium cations being generally preferred in that the quaternary ammonium tetrafluoroborates exhibit good solubility and conductivity in the electrolysis medium and are difficultly reduced.

The term "quaternary ammonium" is employed in its generally recognized sense to mean a cation having four organic groups substituted on the nitrogen.

In accordance with the process of the instant invention, the electrolysis is carried out over a broad range of electrolysis conditions, including a wide range of strengths of applied electric currents and current densities at the electrodes. The process is operable at very low current densities, such as less than 5 milliamperes per square centimeter ($mA/cm^2$) to more than 100 or 200 $mA/cm^2$. In general, it will be recognized that high current densities are advantageously employed in order to maximize electrolysis cell utilization. At the same time, however, this factor favoring high current densities must be balanced against the resultant high electrolysis cell voltage and resistance and heat generation which, in turn, add to costs. Preferred current densities will generally be in the range of from about 15 $mA/cm^2$ to about 50 $mA/cm^2$, with current densities of from about 20 $mA/cm^2$ to about 25 $mA/cm^2$ being most preferred.

The process of the instant invention can be carried out over a broad range of concentrations for the components of the electrolysis medium. The concentration of the dialkyl maleate, for example, is not narrowly critical; it is limited only by the solubility of the dialkyl maleate in the alkanol of the electrolysis medium. It is recognized, however, that the electrical resistance of the electrolysis medium tends to increase with increasing concentrations of components contained in the electrolysis medium. Thus, concentrations of dialkyl maleate from less than about 5% by weight to more than 50% by weight are suitable and result in high selectivities to, and yields of, the desired hydrodimeric product, tetraalkyl 1,2,3,4-butanetetracarboxylate. Preferred concentrations of dialkyl maleate, however, are from at least about 15% by weight to about 40% by weight of the electrolysis medium. Concentrations in the same range of the resultant hydrodimeric product (upon completion of the electrolytic hydrodimeric coupling reaction) also are suitable and preferred.

The concentration of the mixed supporting electrolyte is not narrowly critical and can vary to a substantial degree. Usually, however, it is unnecessary to have more than dilute concentrations for conductivity. Higher concentrations will improve conductivity, but supporting electrolytes of the type suitable for use in the process of the instant invention, in general, are not very soluble in alkanols of the type suitable for use in the process of the instant invention. And there is no advantage in employing amounts of supporting electrolytes in excess of their solubility in the alkanol of choice. Suitable concentrations of the mixed supporting electrolyte will often be in the range of from about 0.5% by weight to about 5% by weight of the electrolysis medium, preferably from about 1.0% by weight to about 3.5% by weight, all at the previously noted alkali metal alkoxide/quaternary ammonium tetrafluoroborate mol ratio of from about 0.5/1 to about 5/1.

The indicated concentration ranges for the dialkyl maleate reactant are, in general, initial concentrations, as the concentration will change during the electrolysis process, which will generally be conducted as a batch reaction, or a series of batch reactions, although the process is not limited only to such batch reaction(s) and can be conducted in a continuous mode.

A continuous mode of operation can involve recirculation of a flowing electrolyte stream between the electrodes, with continuous or intermittent sampling of the stream for product removal. At the same time, the electrolysis medium can be augmented by replenishing depleted components continuously or intermittently, as appropriate, to maintain the desired concentrations of such components.

The electrolysis reaction will ordinarily be conducted at fairly high conversions, e.g., greater than 75% conversion of the dialkyl maleate because selectivity to the desired hydrodimeric product is very good at high conversions. In addition, high conversions avoid unnecessary steps, handling, and expense in separating unreacted dialkyl maleate from the hydrodimeric product for recycle. In a preferred embodiment, the electrolysis is conducted at a dialkyl maleate conversion of about 90% conversion or higher. It has been found, however, that continued electrolysis with little or no dialkyl maleate being present in the electrolysis medium results in increased electrode degradation.

It will be noted that undesired side reactions can occur. For example, it has been found that there is a competing chemical side reaction which produces dimethyl 2-methoxysuccinate [or simply dimethyl methoxysuccinate (MeODMS)]. The extent of the occurrence of this reaction, in general, is dependent upon the time of exposure of the dialkyl maleate reactant to the components of the electrolysis medium or reaction system. As such, it may be desirable to conduct the electrolysis as a series of batch reactions, with a relatively low initial dialkyl maleate concentration and addition of additional dialkyl maleate in subsequent batches of the series. In such a series of batch reactions, the last batch could then be taken to high conversion prior to product separation. Another approach to minimizing dialkyl maleate contact time is to use an electrolysis cell which is large, particularly with respect to electrode surface area, compared to the amount of material in the reaction system and dialkyl maleate reactant. Still another approach is to employ a constant stirred tank reactor with a continuous feed and discharge where the dialkyl maleate concentration is maintained low to diminish the chemical driving force for the undesired competing chemical side reaction.

The control of reaction time can be expressed in terms of electrical current supply. The conversion of a particular amount of dialkyl maleate reactant requires a corresponding number of ampere-hours (A-hr) of current, and the time to accumulate a requisite number of A-hr in an electrolysis can be varied by changing the current and/or the number or size of the electrolysis cell(s). With the foregoing in mind, it will be apparent to one having ordinary skill in the art that if the same electric current is involved, a multiple-cell, e.g., 16-cell, aggregate will accumulate A-hr at a rate equivalent to a corresponding multiple of a lesser cell aggregate. For example, a 16-cell aggregate will accumulate A-hr at a rate twice that of an eight (8)-cell aggregate. At the same time, it is recognized that the greater the number of electrolysis cells contained in the multiple-cell aggregate, the higher will be the voltage required to attain equivalent current.

The particular type of electrolysis cell employed in the process of the instant invention is not critical. The electrolysis cell can consist of a glass container having one or more anodes and cathodes connected to a source of direct electrical current. The electrolysis cell also can consist of the two electrodes separated by an insulator such as a rubber or other non-conducting gasket or spacer. In such an electrolysis cell, which is conveniently described as a "sandwich-type" electrolysis cell, the electrolysis medium is preferably flowed past the (two) parallel electrodes (cathode and anode) in a recirculating system. Such an arrangement allows large volumes of the electrolysis medium to be effectively subjected to electrolysis in a relatively small electrolysis cell having preferred closely-spaced electrode surfaces.

Electrolysis cells for large scale production are contemplated as using at least 5 A, and oftentimes 10 or more A. Taking into consideration the amperage and number of electrolysis cells employed, the instant process will ordinarily use current and dialkyl maleate amounts such that no more than 100 grams (g) of dialkyl maleate are present per cell-A, and preferably less than 50 g, or possibly even less than 25 g.

The term "cell-ampere" (cell-A) is employed herein to mean the number of cells×amperes, and is equivalent to ampere-hours per hour [(A-hr)/hr].

The electrolytic process of the instant invention is effected using graphite (plate, felt, rods, fibers, and the like) electrodes, i.e., both cathode and anode, with graphite plate and felt being particularly advantageous for flow-through sandwich-type electrolysis cell configurations. Additional advantages which are realized from the use of graphite as the electrodes of choice includes high conversions of the dialkyl maleate reactant, as well as high selectivities to, and high yields of, the desired hydrodimeric coupled product, tetraalkyl 1,2,3,4-butanetetracarboxylate. Moreover, graphite is much less expensive than many other known and commonly used electrode materials, such as platinum or even lead or cadmium electrodes and it does not add heavy metals to the electrolysis medium via corrosion.

The temperature at which the process of the instant invention is conducted is not narrowly critical. However, it may be desirable to avoid excessively high or elevated temperatures in that increased production of undesirable by-products may result. Also, it may be desirable to avoid elevated temperatures when a volatile alkanol, e.g., methanol, is employed as a solvent in the electrolysis medium in order to avoid loss of such materials, and various cooling means can be used for this purpose. Cooling to ambient temperatures is generally sufficient, but, if desired, temperatures down to 0° C. or lower can be employed so long as the desired hydrodimeric coupling reaction occurs with reasonable efficiency. For convenience, temperatures in the range from about 0° C. to a temperature not to exceed the boiling point of the alkanol employed as the solvent in the electrolysis medium. For example, when methanol is the alkanol of choice, a convenient maximum temperature is about 60° C. In general, however, temperatures of from about 15° C. to about 50° C. are preferred, with temperatures of from about 20° C. to about 40° C. being most preferred.

The process of the instant invention can be conducted at atmospheric pressure, superatmospheric pressures, and subatmospheric pressures. However, for practical reasons and reasons of economy and construction of equipment, it is preferred to conduct the instant process at approximately atmospheric pressure.

The process of the instant invention can be carried out effectively and efficiently with an alkanol, e.g., methanol, as the only material employed as carrier for the dialkyl maleate reactant and mixed supporting electrolyte. Ordinary industrial grades of the alkanol of choice which are substantially water-free, are very suitable for use. Traces of water picked up from contact with the atmosphere will not ordinarily be sufficient to adversely affect results. For example, 2000 parts per million (ppm) of water in the electrolysis medium has negligible effect. However, the presence of more than traces of water will preferably be avoided, as even a small percentage of water can cause a decline in selectivity, and the presence of more than, say 5% by weight, of water is very undesirable. If desired, co-solvents can be employed along with the alkanol, particularly such aprotic solvents as dimethylformamide, dimethyl sulfoxide, acetonitrile, and mixtures thereof. It is noted, however, that the use of co-solvents generally will not be desirable, although there may be particular circumstances where solubility or other factors would make the use of co-solvents worthwhile and advantageous.

Upon completion of the electrolysis, the tetraalkyl 1,2,3,4-butanetetracarboxylate product is present in solution in the electrolysis medium, e.g., at a concentration of about 25% by weight. Recovery of the tetraalkyl 1,2,3,4-butanetetracarboxylate from the electrolysis medium is effected by cooling the resultant reaction mixture to induce as complete crystallization as possible of the tetraalkyl 1,2,3,4-butanetetracarboxylate product, followed by separation by techniques well known in the art, e.g., filtration, centrifugation, and the like. In the case of tetramethyl 1,2,3,4-butanetetracarboxylate, the crystallization is effected by cooling the resultant reaction mixture, e.g., to less than 0° C., usually between about 0° C. and −10° C. The precipitated crystals are separated from the supernatant liquid by filtration, washed, preferably with the alkanol of choice employed as the solvent for the electrolysis medium, and dried. Recrystallization, if desired, can be effected from a suitable solvent, e.g., the same alkanol of choice.

The separation of the tetraalkyl 1,2,3,4-butanetetracarboxylate product from the resultant reaction mixture effectively separates the product from residual dialkyl maleate reactant and undesirable by-products, e.g., dialkyl succinate and dialkyl 2-alkoxysuccinate.

It will be apparent to those skilled in the art that since the desired tetraalkyl 1,2,3,4-butanetetracarboxylate is a tetraester, it can be subjected to hydrolysis and purification procedures to prepare the corresponding 1,2,3,4-butanetetracarboxylic acid suitable for permanent press use, as described and claimed in commonly assigned U.S. Pat. No. 5,298,653, which reference, as previously noted, is herein incorporated by reference.

The following specific examples illustrating the best currently-known mode of practicing the instant invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

Electrolyses were conducted in a sandwich-type undivided electrolysis flow cell of parallel plate design fitted with graphite plate electrodes, both cathode and anode, having a surface area for each electrode of 114.75 cm$^2$, and with a gap between the electrodes of about 1 millimeter (mm). The electrolysis cell fluid volume capacity was approximately 11.5 cm$^3$ and its flow rate was approximately 0.762 meter/second [m/s; 2.5 feet/second (ft/s)]. The electrolysis cell was connected to a circulating pump and a jacketed, refrigerated reservoir maintained at about 5° C. The chilled reservoir was charged with the desired quantities of dimethyl maleate (DMM), methanol, and supporting electrolyte. The resultant solution was chilled to about 20° C. and subjected to electrolysis while maintaining the temperature at the initial 20° C. The results and parameters are tabulated in Table 1.

In Table 1, the formulas and abbreviations employed, except as otherwise specified, represent designations as follows:

$Bu_4NBF_4$ is tetrabutylammonium tetrafluoroborate; and

NaOMe is sodium methoxide.

TABLE 1

| Example | DMM[1] g | mol | PI[2] | MeOH,g | Supporting Electrolyte | | mmol/ 100.00 g[3] | wt %[4] | mol ratio | Total Charge, g |
|---|---|---|---|---|---|---|---|---|---|---|
| | | | | | g | mmol | | | | |
| 1 | 83.38 | 0.58 | 36.11 | 145.11 | NaOMe 0.49 | 9.074 | 3.92 | 1.24 | 1.26 | 231.39 |
| | | | | | $Bu_4NBF_4$ 2.38 | 7.23 | 3.12 | | 1.00 | |
| 2[10] | 102.08 | 0.71 | 35.92 | 180.19 | NaOMe 1.87 | 34.63 | 12.19 | 0.66 | — | 284.14 |
| 3[10] | 62.00 | 0.43 | 36.03 | 108.37 | $Bu_4NBF_4$ 1.72 | 5.23 | 3.039 | 1.00 | — | 172.09 |

TABLE 1-continued

| Example | CD[5] mA/cm² | RX Time, hr | Conv., mol % | Yield, mol %[6] | | |
| --- | --- | --- | --- | --- | --- | --- |
| | | | | TMBTC[7] | DMS[8] | MeODMS[9] |
| 1 | 25 | 6.92 | 94.46 | 73.93 | 13.80 | 1.080 |
| 2[10] | 25 | 5.00 | 92.46 | 35.31 | 1.42 | 39.12 |
| 3[10] | 25 | 5.05 | 80.74 | 51.11 | 28.39 | 0.62 |

[1]Dimethyl maleate.
[2]Payload in % by weight dimethyl maleate (DMM) in solution
[3]Concentration of indicated supporting electrolyte in millimoles per 100.00 g of solution.
[4]Concentration of total supporting electrolyte in solution in weight %.
[5]Current density in milliamperes/cm² (mA/cm²).
[6]Yield in mol % normalized to 100% conversion of DMM.
[7]Tetramethyl 1,2,3,4-butanetetracarboxylate.
[8]Dimethyl succinate.
[9]Dimethyl 2-methoxysuccinate; or simply dimethyl methoxysuccinate.
[10]Comparative example.

Thus, it is apparent that there has been provided, in accordance with the instant invention, a process that fully satisfies the objects and advantages set forth hereinabove. While the invention has been described with respect to various specific examples and embodiments thereof, it is understood that the invention is not limited thereto and many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the preparation of tetraalkyl 1,2,3,4-butanetetracarboxylate, which process comprises subjecting a substantially anhydrous liquid electrolysis medium containing a dialkyl maleate, an alkanol corresponding to the alkyl groups of the dialkyl maleate, and an alkanol-soluble alkali metal alkoxide/quaternary ammonium tetrafluoroborate supporting electrolyte to electrolysis in an electrolysis cell, using a graphite anode and a graphite cathode, to effect electrohydrodimerization of the dialkyl maleate to yield the tetraalkyl 1,2,3,4-butanetetracarboxylate.

2. The process of claim 1 wherein the dialkyl maleate is present in the electrolysis medium in an initial concentration of from about 5% by weight up to about 50% by weight.

3. The process of claim 2 wherein the initial concentration of the dialkyl maleate in the electrolysis medium is at least about 15% by weight.

4. The process of claim 3 wherein the initial concentration of the dialkyl maleate in the electrolysis medium is from about 15% by weight to about 40% by weight.

5. The process of claim 1 wherein the dialkyl maleate is dimethyl maleate, the alkanol is methanol, and the tetraalkyl 1,2,3,4-butanetetracarboxylate is tetramethyl 1,2,3,4-butanetetracarboxylate.

6. The process of claim 1 wherein the alkali metal alkoxide/quaternary ammonium tetrafluoroborate supporting electrolyte is sodium methoxide/tetrabutylammonium tetrafluoroborate.

7. The process of claim 1 wherein the alkali metal alkoxide/quaternary ammonium tetrafluoroborate supporting electrolyte mol ratio is between about 0.5:1 and about 5:1.

8. The process of claim 7 wherein the alkali metal alkoxide/quaternary ammonium tetrafluoroborate supporting electrolyte mol ratio is about 1:1.

9. The process of claim 1 wherein the supporting electrolyte is present in the electrolysis medium at a concentration of from about 0.5% by weight to about 5.0% by weight.

10. The process of claim 9 wherein the concentration of the supporting electrolyte in the electrolysis medium is from about 1.0% by weight percent to about 3.5% by weight.

11. The process of claim 1 wherein the electrolysis is conducted at a temperature less than the boiling point of the alkanol.

12. The process of claim 11 wherein the temperature is from about 15° C. to about 50° C.

13. The process of claim 12 wherein the temperature is from about 20° C. to about 40° C.

14. The process of claim 1 wherein the electrolysis is continued until at least about 75% of the dialkyl maleate has reacted.

15. The process of claim 1 wherein the electrolysis is conducted at current densities of at least about 15 mA/cm².

16. The process of claim 15 wherein the current densities are in the range from about 15 mA/cm² to about 100 mA/cm².

17. The process of claim 1 wherein the tetraalkyl 1,2.3,4-butanetetracarboxylate is recovered from the electrolysis medium by cooling to induce crystallization, followed by separation.

18. The process of claim 17 wherein the separation is effected by a technique selected from the group consisting of filtration and centrifugation.

19. The process of claim 18 wherein the separation is effected by filtration.

* * * * *